United States Patent
Riva et al.

(10) Patent No.: US 6,452,018 B1
(45) Date of Patent: Sep. 17, 2002

(54) 2-(2'-HYDROXYPHENYL) BENZOTRIAZOLES CONTAINING A 2,4-IMIDAZOLIDINEDIONE GROUP AND PROCESS FOR THEIR PREPARATION

(75) Inventors: Rosa Maria Riva, Merate; Carlo Neri, S. Donato Milanese; Barbara Granelli, Casalpusterlengo, all of (IT)

(73) Assignee: Great Lakes Chemical Italia S. r. L., Milan (IT)

( * ) Notice: Subject to any disclaimer, the term of this patent is extended or adjusted under 35 U.S.C. 154(b) by 0 days.

(21) Appl. No.: 09/600,861

(22) PCT Filed: Jan. 25, 1999

(86) PCT No.: PCT/EP99/00345

§ 371 (c)(1),
(2), (4) Date: Jul. 27, 2000

(87) PCT Pub. No.: WO99/37638

PCT Pub. Date: Jul. 29, 1999

(30) Foreign Application Priority Data

Jan. 27, 1998 (IT) .......................................... MI98A0138

(51) Int. Cl.[7] .......................................... C07D 249/20
(52) U.S. Cl. ........................ 548/261; 548/259; 548/260
(58) Field of Search ................................. 548/259, 260, 548/261

(56) References Cited

U.S. PATENT DOCUMENTS

| | | |
|---|---|---|
| 3,399,173 A | 8/1968 | Heller et al. |
| 4,044,019 A | 8/1977 | Schmidt et al. |
| 4,069,197 A | 1/1978 | Rosenberger et al. |
| 4,948,666 A | 8/1990 | Paul et al. |
| 5,233,047 A | 8/1993 | MacLeay et al. |
| 5,488,112 A * | 1/1996 | Reinehr et al. ............ 548/261 |

FOREIGN PATENT DOCUMENTS

| | | |
|---|---|---|
| EP | 0669330 | 8/1995 |
| EP | 0867435 | 9/1998 |

* cited by examiner

*Primary Examiner*—Patricia L. Morris
(74) *Attorney, Agent, or Firm*—Oblon, Spivak, McClelland, Maier & Neustadt, P.C.

(57) ABSTRACT

2-(2'-hydroxyphenyl)benzotriazoles having general formula (I). The above 2-(2'-hydroyzphenyl)benzotriazoles having general formula (I) are useful as heat, oxygen and light stabilizers for organic polymers. In particular they are useful as UV stabilizers for organic polymers.

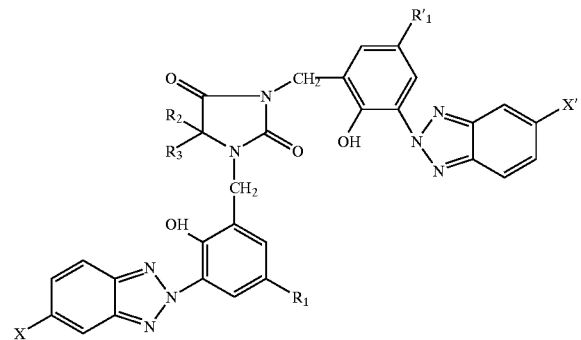

12 Claims, No Drawings

2-(2'-HYDROXYPHENYL) BENZOTRIAZOLES CONTAINING A 2,4-IMIDAZOLIDINEDIONE GROUP AND PROCESS FOR THEIR PREPARATION 2-(2'-hydroxyphenyl)benzotriazoles having general formula (I):

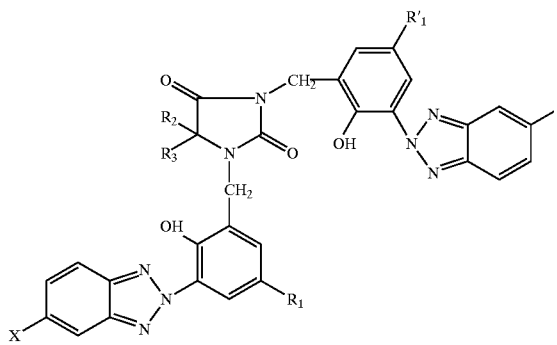

(I)

The above 2-(2'-hydroxyphenyl)benzotriazoles having general formula (I) are useful as heat, oxygen and light stabilizers for organic polymers. In particular they are useful as UV stabilizers for organic polymers.

The present invention relates to 2-(2'-hydroxyphenyl)benzotriazoles containing a 2,4-imidazolidinedione group.

More specifically, the present invention relates to 2-(2'-hydroxyphenyl)benzotriazoles containing a 2,4-imidazolidinedione group or a 2,4-imidazolidinedione-5,5-disubstituted group in the molecule, a process for their preparation and their use as light stabilizers for organic polymers.

The present invention also relates to the polymeric compositions stabilized with the above benzotriazoles and to the end-products obtained from these compositions.

2-(2'-hydroxyphenyl)benzotriazoles which can be used as light stabilizers are known in the art. These benzotriazoles however have various disadvantages. In fact, they are often rather volatile, they have a low thermal stability and, as they sometimes have an absorption at 400 nm, they give the polymers, into which they are incorporated, a yellow colouring.

The Applicant has now surprisingly found that 2-(2'-hydroxyphenyl)benzotriazoles containing a 2,4-imidazolidinedione group or a 2,4-imidazolidinedione-5,5-disubstituted group in the molecule, are capable of overcoming the drawbacks of the known art. In fact, the above benzotriazoles have a low volatility (they are therefore able to remain inside the stabilized organic polymer for a longer period) and also a high thermal stability. In addition, they have a low absorption ("cut-off") at $\lambda=400$ nm and an excellent absorption at $\lambda=302$ nm and at $\lambda=340$ nm and consequently they do not give a yellow colouring to the polymers into which they are incorporated.

The present invention therefore relates to 2-(2'-hydroxyphenyl)benzotriazoles having general formula (I):

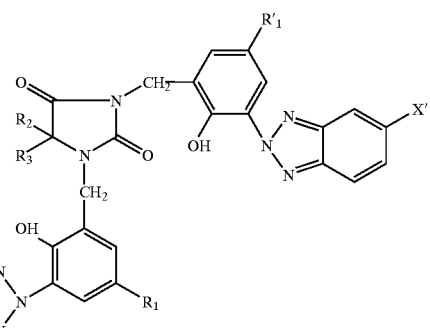

(I)

wherein:

X and X', the same or different, represent a hydrogen atom; a halogen atom selected from chlorine and bromine; a linear or branched $C_1-C_{18}$ alkyl group; a linear or branched $C_1-C_{18}$ alkoxyl group; a cyano group;

$R_1$ and $R'_1$, the same or different, represent a halogen atom selected from chlorine and bromine; a linear or branched $C_1-C_{18}$ alkyl group; a linear or branched $C_2-C_{18}$ alkenyl group; a linear or branched $C_2-C_{18}$ alkinyl group; a $C_5-C_{18}$ cycloalkyl group, said cycloalkyl group optionally substituted; a $C_7-C_{15}$ arylalkyl or alkylaryl group; a $C_6-C_{14}$ aryl group, said aryl group optionally substituted; a linear or branched $C_1-C_{18}$ alkoxyl group; a heterocyclic group with 5 or 6 atoms containing at least one heteroatom selected from oxygen, nitrogen and sulfur, said heterocyclic group optionally substituted; a group having the formula:

1a:

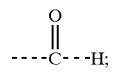

a —$COR_4$ group or a —$NR_5R_6$ group wherein $R_4$, $R_5$ and $R_6$, the same or different, represent a linear or branched $C_1-C_{18}$ alkyl group; a linear or branched $C_2-C_{18}$ alkenyl group; a linear or branched $C_2-C_{18}$ alkinyl group; a $C_5-C_{18}$ cycloalkyl group, said cycloalkyl group optionally substituted; a $C_7-C_{15}$ arylalkyl or alkylaryl group; a $C_6-C_{14}$ aryl group, said aryl group optionally substituted; a heterocyclic group with 5 or 6 atoms containing at least one heteroatom selected from oxygen, nitrogen and sulfur, said heterocyclic group optionally substituted;

or $R_1$ and $R'_1$, the same or different, represent an ester group having general formula (II), (III) or (IV):

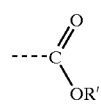

(II)

-continued

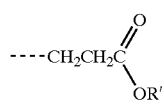
(III)

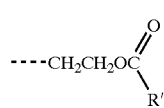
(IV)

or an amide group having general formula (V):

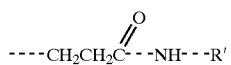
(V)

wherein R' represents a linear or branched $C_1$–$C_{18}$ alkyl group; a linear or branched $C_2$–$C_{18}$ alkenyl group; a linear or branched $C_2$–$C_{18}$ alkinyl group; a $C_5$–$C_{15}$ cycloalkyl group, said cycloalkyl group optionally substituted; a $C_7$–$C_{15}$ arylalkyl or alkylaryl group; a $C_6$–$C_{14}$ aryl group, said aryl group optionally substituted; a linear or branched $C_1$–$C_{18}$ alkoxyl group; a heterocyclic group with 5 or 6 atoms containing at least one heteroatom selected from oxygen, nitrogen and sulfur, said heterocyclic group optionally substituted; or $R_1$ and $R'_1$, the same or different, represent a 4,4'-ethylidenebisphenol group having formula (VI):

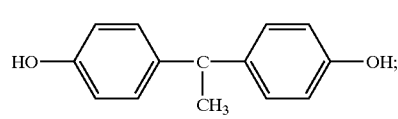
(VI)

$R_2$ and $R_3$, the same or different, represent a hydrogen atom; a linear or branched $C_1$–$C_{18}$ alkyl group; a phenyl group; a heterocyclic group with 5 or 6 atoms containing at least one heteroatom selected from oxygen, nitrogen and sulfur, said heterocyclic group optionally substituted.

The compounds having general formula (I) can be used as heat, oxygen and light stabilizers for organic polymers. In particular they are useful as UV stabilizers for organic polymers.

When the $C_5$–$C_{18}$ cycloalkyl groups, the $C_6$–$C_{14}$ aryl groups and the heterocyclic groups with 5 or 6 atoms are defined as being optionally substituted, these groups are substituted with: halogen atoms selected from chlorine and bromine, linear or branched $C_1$–$C_{18}$ alkyl groups, linear or branched $C_2$–$C_{18}$ alkenyl groups; linear or branched $C_2$–$C_{18}$ alkinyl groups, OH groups, NH groups, SH groups.

Examples of $C_1$–$C_{18}$ alkyl groups are: methyl, ethyl, propyl, isopropyl, n-butyl, sec-butyl, t-butyl, t-amyl, 2-ethylhexyl, n-octyl, 1,1,3,3-tetramethylbutyl, n-dodecyl, 1,1,7,7-tetramethyloctyl, n-octadecyl, etc.

Examples of $C_2$–$C_{18}$ alkenyl groups are: vinyl, propylene, butylene, pentylene, hexylene, etc.

Examples of $C_2$–$C_{18}$ alkinyl groups are: acetylene, propyne, butyne, 2-butyne, etc.

Examples of $C_5$–$C_{18}$ cycloalkyl groups, optionally substituted, are: cyclohexyl, cyclopentyl, methylcyclohexyl, etc.

Examples of $C_7$–$C_{115}$ arylalkyl or alkylaryl groups are: benzyl, 2-phenylethyl, 4-t-butylbenzyl, etc.

Examples of $C_6$–$C_{14}$ aryl groups, optionally substituted, are: phenyl, naphthyl, anthracenyl, 2-hydroxyphenyl, etc.

Examples of $C_1$–$C_{18}$ alkoxyl groups are: methoxyl, ethoxyl, propoxyl, n-butoxyl, etc.

Examples of heterocyclic groups with 5 or 6 atoms, optionally substituted, are: piperidine, morpholine, piperazine, triazole, tetramethylpiperidine, pentamethylpiperidine, tetramethylmorpholine, pentamethylmorpholine, 4-hydroxy-tetramethylpiperidine, etc.

Specific examples of compounds having general formula (I), which in no way limit the scope of the present invention, are:

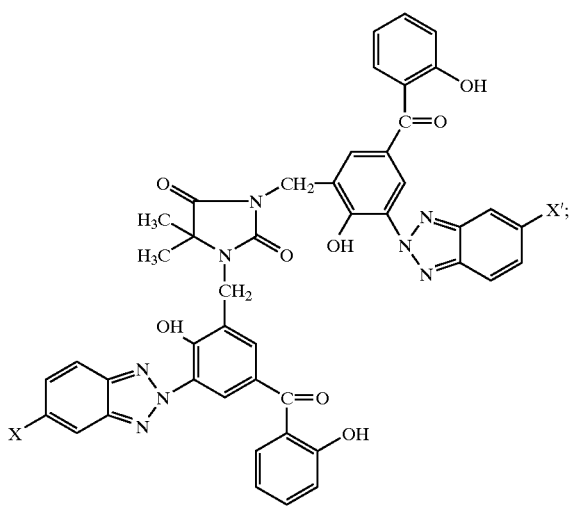
(Ia)

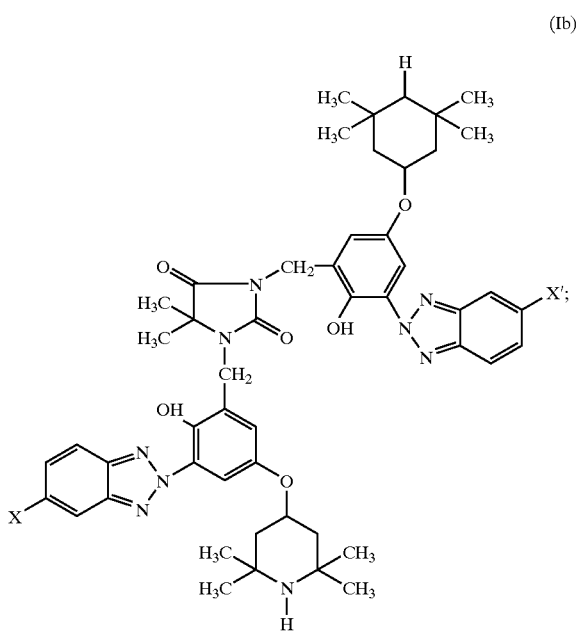
(Ib)

(Ic)

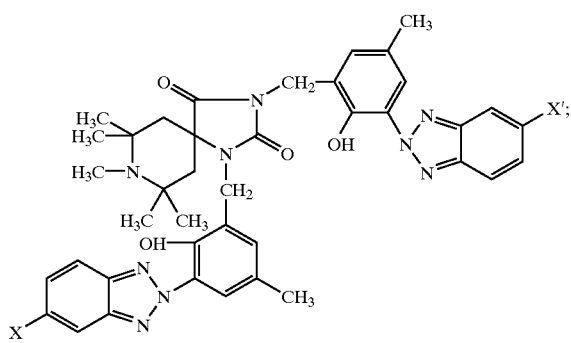

wherein X and X' have the same meanings described above.

The compounds having general formula (I) of the present invention can be prepared with various processes.

A further object of the present invention relates to a process for the preparation of 2-(2'-hydroxyphenyl) benzotriazoles having general formula (I).

A process for the preparation of compounds having general formula (I) consists in reacting a 2-(2'-hydroxyphenyl) benzotriazole having general formula (VIIA) or (VIIB):

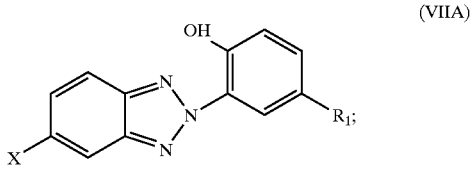

(VIIA)

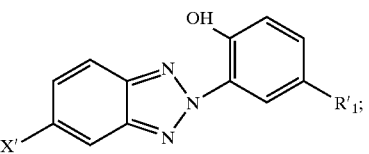

(VIIB)

wherein X, X', $R_1$ and $R'_1$ have the same meanings described above, with a 2,4-imidazolidinedione-1-monomethylol having general formula (VIII):

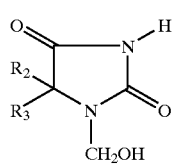

(VIII)

wherein $R_2$ and $R_3$ have the same meanings described above, in the presence of concentrated sulfuric acid, for example, at a concentration ranging from 70% to 98%, at a temperature ranging from −5° C. to +30° C. The intermediate compound having general formula (IXA) or (IXB), is isolated from the raw product thus obtained:

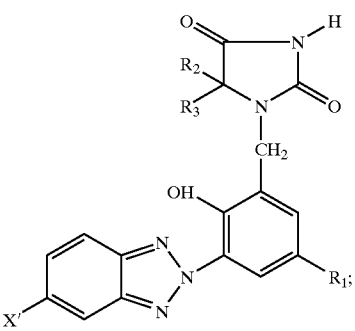

(IXA)

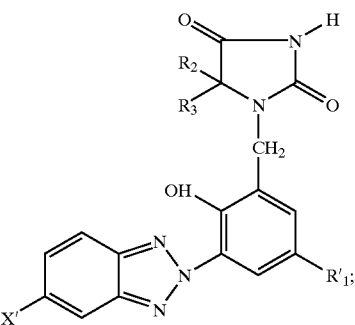

(IXB)

wherein X, X', $R_1$ and $R'_1$ have the same meanings described above, operating according to processes known in the art such as, for example, by adding the raw product to water, preferably water-ice, dropwise and removing the solid obtained by filtration followed by washing and crystallization in the presence of inert organic solvents.

Inert organic solvents which can be used for effecting the above crystallization are: linear or cyclic aliphatic hydrocarbons such as, for example, hexane, heptane, n-octane, cyclohexane, methyl-cyclohexane, etc.; aromatic hydrocarbons such as, for example, toluene, etc.; alcohols such as, for example, methanol, isopropanol, etc.; chlorinated aromatic solvents such as, for example, chlorobenzene, etc.; ketones such as, for example, methylisobutylketone, etc.; monoalkyl ethers of ethylene glycol such as, for example, 2-methoxyethanol (methyl cellosolve), etc.

When in the 2-(2'-hydroxyphenyl)benzotriazoles having general formula (I), $R_1$ or $R'_1$ represent an ester group having general formula (II), (III) or (IV), or represent an amide group having general formula (V), the reaction between the 2-(2'-hydroxyphenyl)benzotriazole having general formula (VIIA) or (VIIB) described above with 2,4-imidazolidinedione-1-monomethylol having general formula (VIII) described above, must be carried out without sulfuric acid. This reaction is carried out in the presence of toluene and p-toluenesulfonic acid as catalyst, at a temperature ranging from room temperature to the boiling point of toluene.

The intermediate having general formula (IXA) or (IXB) obtained as described above, is reacted with formaldehyde, in the presence of an alkaline catalyst such as, for example, sodium carbonate, sodium hydrogen carbonate, etc., in the presence of an inert organic solvent such as, for example, methanol, etc., at a temperature ranging from 50° C. to 65° C., obtaining the compound having general formula (XA) or (XB):

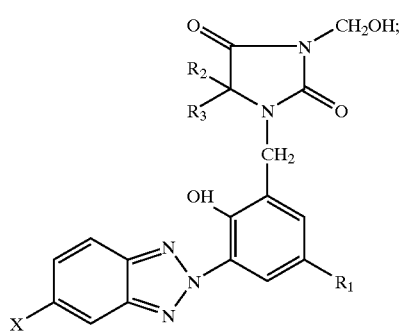

(XA)

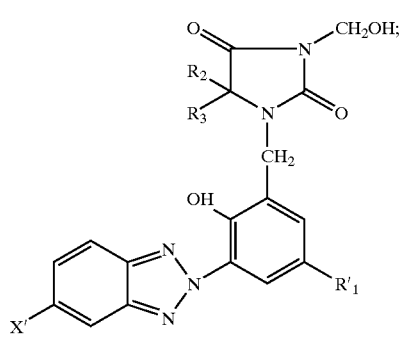

(XB)

wherein X, X', $R_1$ and $R'_1$ have the same meanings described above. This compound having general formula (XA) or (XB) is reacted with a compound having general formula (VIIA) or (VIIB) described above obtaining the desired compound having general formula (I): the reaction conditions and the isolation conditions of the compound having general formula (I) are the same as those described above relating to the reaction of the compound having general formula (VIIA) or (VIIB) with 2,4-imidazolidinedione-1-monomethylol having general formula (VIII).

The 2-(2'-hydroxyphenyl)benzotriazoles having general formula (VIIA) and (VIIB) can be prepared as described, for example, in German patent application DE 4.237.817.

The 2,4-imidazolidinedione-1-monomethylol having general formula (VIII) can be prepared as described, for example, in Rumenian patent RO 72.413; or as described, for example, in Chemical Abstract (1982) 96, 199694q.

Alternatively, the compounds having general formula (I) of the present invention can be prepared by the reaction of a 2-(2'-hydroxy-3-hydroxymethylphenyl)benzotriazole having general formula (XIA) or (XIB):

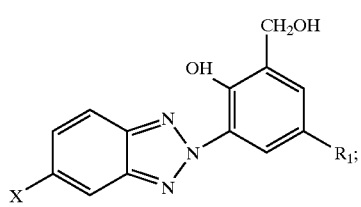

(XIA)

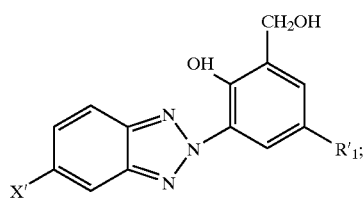

(XIB)

wherein X, X', $R_1$ and $R'_1$ have the same meanings described above, with a 2,4-imidazolidinedione having general formula (XII):

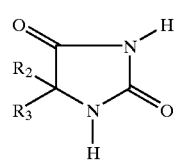

(XII)

wherein $R_2$ and $R_3$ have the same meanings described above, obtaining the desired compound having general formula (I): the reaction conditions and the isolation conditions of the compound having general formula (I) are the same as those described above relating to the reaction of the compound having general formula (VIIA) or (VIIB) with 2,4-imidazolidinedione-1-monomethylol having general formula (VIII).

The 2-(2'-hydroxy-3-hydroxymethylphenyl) benzotriazoles having general formula (XIA) or (XIB), can be prepared as described, for example, in Czechoslovak patent application CS 164.138.

The 2,4-imidazolidinediones having general formula (XII) are commercially available.

As already mentioned above, the compounds having general formula (I) of the present invention can be used as heat, oxygen and light stabilizers for a wide range of organic polymers.

Organic polymers capable of being stabilized with the compounds of the present invention are:

(1) polymers of mono-olefins and diolefins such as, for example, polypropylene, polyisobutylene, polybut-1-ene, poly-4-methylpent-1-ene, polyisoprene or polybutadiene; as well as polymers of cyclo-olefins such as, for example, cyclopentene or norbornene; polyethylene (which can be optionally cross-linked) such as, for example, high density polyethylene (HDPE), low density polyethylene (LDPE), linear low density polyethylene (LLDPE), branched low density polyethylene (BLDPE).

Polyolefins such as, for example the monolefins mentioned in the above paragraph, preferably polyethylene and polypropylene, can be prepared with various methods known in literature, preferably using the following methods:

(a) radicalic polymerization (generally carried out at a high pressure and high temperature);

(b) catalytic polymerization using a catalyst which normally contains one or more metals of groups IVb, Vb, VIb or VIII of Periodic Table. These metals generally have one or more ligands such as, for example, oxides, halides, alcoholates, ethers, amines, alkyls, alkenyls and/or aryls which can be π, or σ-co-ordinated. These metal complexes can be in free form or supported in substrates such as, for example activated magnesium chloride, titanium(III) chloride, alumina or silicon oxide. These catalysts can be soluble or insoluble in the reaction medium. The catalysts can be used alone or in the presence of other activators such as, for example, metal alkyls, metal hydrides, halides of metal alkyls, oxides of metal alkyls or metal alkyloxanes, these metals being elements belonging to groups Ia, IIa and/or IIIa of the Periodic Table. The activators can be conveniently modified with other ester, ether, amine or silyl-ether groups. These catalytic systems are usually called Phillips, Standard Oil Indiana, Ziegler(-Natta), TNZ (Du-Pont), metallocene or "single site catalyst" (SSC).

(2) Mixtures of the polymers described under point (1) such as, for example, mixtures of polypropylene with polyisobutylene; mixtures of polypropylene with polyethylene (for example, PP/HDPE, PP/LDPE); mixtures of different types of polyethylene (for example, LDPE/HDPE).

(3) Copolymers of mono-olefins and diolefins with each other or with other vinyl monomers such as, for example, ethylene-propylene copolymers, linear low density polyethylene (LLDPE) and its mixtures with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with polypropylene and a diene such as, for example, hexadiene, dicyclopentadiene or ethylidene-norbornene; and mixtures of these copolymers with each other or with the polymers cited in paragraph (1) such as, for example, polypropylene/ethylene-propylene copolymers, LDPE/ethylene-vinylacetate (EVA) copolymers, LDPE/ethylene-acrylic acid (EAA) copolymers, LLDPE/EVA, LLDPE/EAA, and alternating or "random" polyalkylene/carbon monoxide copolymers and their mixtures with other polymers such as, for example, polyamides.

(4) Hydrocarbon resins (for example, $C_5$–$C_9$) comprising their hydrogenated modifications (for example, adhesive agents) and mixtures with polyalkylene and starch.

(5) Polystyrene, poly (p-methylstyrene), poly(α-methylstyrene).

(6) Copolymers of styrene or α-methylstyrene with dienes or acrylic derivatives such as, for example, styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methylacrylate; mixtures, having a high impact strength, between copolymers of styrene and another polymer such as, for example, a polyacrylate, a polymer of a diene or an ethylene/propylene/diene terpolymer, block polymers of styrene such as, for example, styrene/butadiene/styrene, styrene/isoprene/styrene, styrene/ethylene/butylene/styrene or styrene/ethylene/propylene/styrene.

(7) Grafted copolymers of styrene or α-methylstyrene such as, for example, styrene in polybutadiene, styrene in polybutadiene or polybutadiene-acrylonitrile copolymers; styrene and acrylonitrile (or methacrylonitrile) in polybutadiene; styrene, acrylonitrile and methylmethacrylate in polybutadiene; styrene and maleic anhydride in polybutadiene; styrene, acrylonitrile and maleic anhydride or maleimide in polybutadiene; styrene and maleimide in polybutadiene; styrene and alkylacrylates or methacrylates in polybutadiene; styrene and acrylonitrile in ethylene/propylene/diene terpolymers, styrene and acrylonitrile in polyalkyl acrylates or polyalkyl methacrylates, styrene and acrylonitrile in acrylate/butadiene copolymers, as well as mixtures of the copolymers listed above with the copolymers cited under point (6) such as, for example, mixtures of known copolymers such as ABS, MBS, ASA or AES.

(8) Polymers containing halogens such as, for example, polychloroprene, chlorinated rubbers, chlorinated or chlorosulfonated polyethylene, ethylene and chlorinated ethylene copolymers, homopolymers and copolymers of epichlorohydrin, in particular polymers of vinyl compounds containing halogens such as, for example, polyvinyl chloride, polyvinylidenechloride, polyvinyl fluoride or polyvinylidenefluoride; and also their copolymers such as, for example, vinyl chloride/vinylidenechloride, vinyl chloride/vinyl acetate or vinylidenechloride/vinyl acetate.

(9) Polymers deriving from α,β-unsaturated acids and their derivatives such as, for example, polyacrylates and polymethacrylates, polymethyl methacrylates, polyacrylamides and polyacrylonitriles, modified with butyl acrylate.

(10) Copolymers of monomers according to point (9) with each other or with other unsaturated monomers such as, for example, acrylonitrile/butadiene copolymers, acrylonitrile/alkylacrylate copolymers, acrylonitrile/alkoxyalkyl acrylate copolymers or acrylonitrile/vinyl halide copolymers or acrylonitrile/alkyl methacrylate/butadiene terpolymers.

(11) Polymers deriving from unsaturated alcohols and amines, or their acyl or acetal derivatives such as, for example, polyvinyl alcohol, polyvinyl acetate, polyvinyl stearate, polyvinyl benzoate, polyvinyl maleate, polyvinyl butyrral, polyallyl phthalate or polyallyl melamine; and also their copolymers with the olefins listed under point (1).

(12) Homopolymers and copolymers of open-chain ethers or cyclic ethers such as, for example, polyalkylene glycols, polyethyleneoxide, polypropylene oxide, or copolymers of the compounds described above with bis-glycidyl ethers.

(13) Polyacetals such as, for example, polyoxymethylene and polyoxymethylenes which contain ethylene oxide as comonomer; polyacetals modified with thermoplastic polyurethanes, acrylates or MBS.

(14) Polyphenylene oxides and sulfides and mixtures of polyphenylene oxides with styrene or polyamide polymers.

(15) Polyurethanes deriving from hydroxyl-terminated polyethers, polyesters or polybutadienes on the one hand and aliphatic or aromatic polyisocyanates on the other, as well as the precursors of the above compounds.

(16) Polyamides and copolyamides deriving from diamines and dicarboxylic acids and/or aminocarboxylic acids or from the corresponding lactams such as, for example, polyamide 4, polyamide 6, polyamide 6/6, 6/10, 6/9, 6/12, 4/6, 12/12, polyamide 11, polyamide 12, aromatic polyamides obtained starting from m-xylene diamine and adipic acid; polyamides prepared from hexamethylenediamine and isophthalic and/or terephthalic acid and with or without an elastomer as modifier, for example, poly-2,4,4-trimethylhexamethylene terephthalamide or poly-m-phenylene isophthalamide; and also block copolymers of the above polyamides with polyolefins, olefinic copolymers, ionomers or elastomers chemically bound or grafted; or with polyethers such as, for example, polyethylene glycol, polypropylene glycol or polytetramethylene glycol; as well as polyamides or copolyamides modified with EPDM or ABS; and polyamides condensed during processing ("RIM polyamide system").

(17) Polyureas, polyimides, polyamide-imides and polybenzoimidazoles.

(18) Polyesters deriving from dicarboxylic acids and diols and/or from hydroxycarboxylic acids or from the corresponding lactones such as, for example, polyethylene terephthalate, polybutylene terephthalate, poly-1,4-dimethylolcyclohexane terephthalate and polyhydroxybenzoates, as well as block copolyether esters deriving from polyethers with hydroxyl-terminated groups; and also polyesters modified with polycarbonates or MBS.

(19) Polycarbonates and polyester carbonates.

(20) Polysulfones, polyethersulfones and polyetherketones.

(21) Cross-linked polymers deriving from aldehydes on the one hand and from phenols, urea and melamines on the other, such as, for example, phenol/formaldehyde resins, urea/formaldehyde resins and melamine/formaldehyde resins.

(22) Drying or non-drying alkyd resins.

(23) Resins based on unsaturated polyesters deriving from copolyesters of dicarboxyl acids saturated and unsaturated with polyhydric alcohols and vinyl compounds as cross-linking agents, and also the above resins containing halogens and having a good flame-resistance.

(24) Cross-linkable acrylic resins deriving from substituted acrylates such as, for example, epoxy acrylates, urethane acrylates or polyester acrylates.

(25) Alkyd resins, resins based on polyesters or acrylated resins cross-linked with melamine resins, urea resins, resins based on polyisocyanates or epoxy resins.

(26) Cross-linked epoxy resins deriving from polyepoxides such as, for example, bis-glycidyl ethers or cycloaliphatic diepoxides.

(27) Natural polymers such as, for example, cellulose, rubber, gelatine, and their derivatives chemically modified to give homologous polymers such as, for example, cellulose acetates, propionates and butyrates, or cellulose ethers such as, for example, methyl-cellulose; as well as hydrocarbon resins ("rosins") or their derivatives.

(28) Mixtures of the above polymers ("polyblends") such as, for example, PP/EPDM, polyamides/EPDM or ABS, PVC/EVA, PVC/ABS, PVC/MBS, PC/ABS, PBTP/ABS, PC/ASA, PC/PBT, PVC/CPE, PVC/acrylates, POM/thermoplastics PUR, PC/thermoplastics PUR, POM/acrylates, POM/MBS, PPO/HIPS, PPO/PA 6.6 and copolymers, PA/HDPE, PA/PP, PA/PPO.

The compounds having formula (I) of the present invention are particularly useful in the stabilization of polycarbonates.

A further object of the present invention relates to polymeric compositions containing an organic polymer and an effective quantity of one or more compounds having general formula (I).

The compounds having general formula (I) of the present invention can be used as such or combined with other stabilizers, in the above polymeric compositions.

In general, the above compounds having general formula (I) are used in a quantity ranging from about 0.1% to about 15% by weight of the weight of the polymeric compositions to be stabilized, although the quantity used varies according to the substrate to be stabilized and the final application. They are preferably added in a quantity ranging from about 0.5% to about 3% by weight of the weight of the polymeric compositions to be stabilized.

The compounds having general formula (I), optionally in the presence of other additives, can be easily incorporated in the organic polymers to be stabilized using the conventional techniques. This incorporation can take place before or during the formation of the end-product, for example, by mixing the compounds having general formula (I) in powder form with the polymer to be stabilized, or by adding these compounds to the polymer to be stabilized in the molten state or in solution, or applying a solution or suspension of these compounds to the polymer to be stabilized, optionally evaporating the solvent used.

The elastomers can be stabilized as latexes. Another method for incorporating the compounds having general formula (I) in the organic polymers comprises the addition of these before or during the polymerization of the corresponding monomers or before the cross-linking.

The compounds having general formula (I) or their mixtures, can be added to the polymer to be stabilized also in masterbatch form which comprises these compounds in a concentration ranging, for example, from 2.5% to 25% by weight.

The compounds having general formula (I) can be conveniently incorporated in the organic polymers to be stabilized by means of the following methods:

in the form of emulsion or suspension (for example, in the case of latexes or polymers in emulsion);

as a mixture of powders in the case of the conventional addition of additional compounds or mixtures of organic polymers;

directly adding to the apparatus used for processing the organic polymers (for example, extruders, internal mixers, etc.);

in the form of solution or molten product.

The polymeric compositions stabilized as described above can be converted to end-products such as, for example, fibers, films, tapes, sheets, multi-layer sheets, containers, tubes and other forms, by means of methods known in the art such as, for example, casting, hot moulding, spinning, extrusion or injection moulding.

The present invention therefore also relates to the use of the above polymeric compositions for the production of end-products.

The use of multi-layer systems is also of interest, in which one of the above compositions having a relatively high content of a compound having general formula (I), for example, between 5% and 15% by weight, is applied in the form of a thin film (10–100 μm in thickness) to a shaped article consisting of a polymer not containing or containing a small quantity of a compound having general formula (I). This application can be carried out during the formation of said article, for example, by means of a co-extrusion. The application can also be effected however on the end shaped-article, for example, by lamination with a film or by coating with a solution. The surface layer or layers of the end-article act as a UW filter which protects the inside of the articles from the deteriorating action of UV light. The upper layer preferably contains from 5% to 15% by weight, more preferably from 5% to 10% by weight, of at least one compound having general formula (I).

The use of the above compositions for the production of multi-layer systems, in which the upper layer having a thickness of 10–100 μm comprises these compositions, whereas the internal layer does not contain or contains a small quantity of a compound having general formula (I) consequently represents a further object of the present invention.

The polymers stabilized as described above have a high resistance to degradation caused by atmospheric agents, in particular a high resistance to UV light. They are therefore capable of maintaining their colour and brightness for a long period even when exposed to external agents.

The compositions described above can also be used as compositions for coating or painting ("coating compositions") such as, for example, paints, lacquers, plastic-based compositions.

For the purposes of the present invention, coating or painting compositions are preferred in which the organic polymer is selected from:
  (a) a thermoplastic polymer selected from thermoplastic polymers containing heteroatoms, in particular nitrogen, sulfur and/or oxygen, in the main chain, styrene copolymers, grafted styrene polymers and polymethyl methacrylates (PMMA); or
  (b) a paint ligand.

Specific examples of thermoplastic polymers (a) containing heteroatoms, in particular nitrogen, sulfur and/or oxygen, in the main chain, are listed above under points 13 to 20. Among these, polycarbonates, polyesters, polyamides, polyacetals, polyphenylene oxides and polyphenylene sulfides are preferred; particularly preferred are polycarbonates, polyesters such as, for example, polyethylene terephthalate (PET), and polyamides (PA) such as, for example, PA 6 and PA 6/6; even more preferred are polycarbonates.

Specific examples of styrene copolymers and grafted styrene polymers (a) are listed above under points 6 and 7.

Paint ligands (b) can comprise at least one of the organic polymers specified herebelow. Specific examples of paints containing specific ligands are:
  1. paints based on alkyd resins, acrylic resins, polyester resins, epoxy resins or melamine resins, which can be cross-linked at a low or high temperature, or mixtures of these resins, to which a cross-linking agent is optionally added;
  2. polyurethane paints with two components based on acrylic resins containing hydroxyl groups, polyester resins or polyether resins and aliphatic or aromatic isocyanates, isocyanurates or polyisocyanates;
  3. polyurethane paints with one component based on block isocyanates, isocyanurates or polyisocyanates which are unblocked during oven treatment;
  4. paints with two components based on (poly)ketoimines and aliphatic or aromatic isocyanates, isocyanurates or polyisocyanates;
  5. paints with two components based on (poly)ketoimines and an unsaturated acrylic resin or a polyacetoacetate resin or a methyl methalcrylamidoglycolate;
  6. paints with two components based on polyacrylates containing a carboxylic group or an amine group and polyepoxides;
  7. paints with two components based on acrylic resins containing an anhydride group and a polyhydroxyl or polyamine compound;
  8. paints with two components based on (poly)oxazoline and acrylic resins containing an anhydride group or unsaturated acrylic resins or aliphatic or aromatic isocyanates, or isocyanurates or polyisocyanates;
  9. paints with two components based on unsaturated polyacrylates and polymalonates;
  10. thermoplastic polyacrylic paints based on thermoplastic acrylic resins or non-self-crosslinkng acrylic resins combined with etherified melamine resins;
  11. systems for paints based on siloxane-modified acrylic resins; 12. systems for paints based on fluoro-modified acrylic resins; and
  13. systems for paints based on allyl glycidyl ethers.

The paints can be applied as one or two layers of coating ("one- or two-coat") and the stabilizing compounds having formula (I) are preferably added to the upper colourless coating.

The paints can be applied to the substrate (metal, plastic, wood, etc.) using the conventional methods such as, for example, brushing, spraying, pouring, dipping or electrophoresis.

A preferred embodiment of the present invention consists in paints or coatings (for example car coatings) comprising at least one compound having general formula (I).

Ligands which can be used for the purpose are, for example, those listed above.

The compounds having general formula (I) of the present invention can be combined, as already mentioned above, with other conventional additives or their mixtures. These additives are added in a quantity ranging from about 0.1% to about 5% by weight of the weight of the polymeric compositions to be stabilized, preferably from about 0.5% to about 3% by weight. Some of the additives used are listed below as an example.

1. Antioxidants
  1.1 Alkylated monophenols such as, for example:

2,6-di-t-butyl-4-methylphenol;
2-t-butyl-4,6-dimethylphenol;
2,6-di-t-butyl-4-ethylphenol;
2,6-di-t-butyl-4-n-butylphenol;
2,6-di-t-butyl-4-isobutylphenol;
2,6-di-cyclopentyl-4-methylphenol;
2-(α-methylcyclohexyl)-4,6-dimethylphenol;

2,6-dioctadecyl-4-methylphenol;
2,4,6-tricyclohexylphenol;
2,6-di-t-butyl-4-methoxymethylphenol;
2,6-di-nonyl-4-methylphenol;
2,4-dimethyl-6-(1'-methylundec-1'-yl)phenol;
2,4-dimethyl-6-(1'-methylhectadec-1'-yl)phenol;
2,4-dimethyl-6-(1'-methyltridec-1'-yl)phenol; and their mixtures.

1.2 Alkylthiomethylphenols such as, for example:

2,4-dioctylthiomethyl-6-t-butylphenol;
2,4-dioctylthiomethyl-6-methylphenol;
2,4-dioctylthiomethyl-6-ethylphenol;
2,6-didodecylthiomethyl-4-nonylphenol.

1.3 Hydroquinones and alkylated hydroquinones such as, for example:
2,6-di-t-butyl-4-methoxyphenol;
2,5-di-t-butylhydroquinone;
2,5-di-t-amylhydroquinone;
2,6-diphenyl-4-octadecyloxyphenol;
2,6-di-t-butylhydroquinone;
2,5-di-t-butyl-4-hydroxyanisol;
3,5-di-t-butyl-4-hydroxyanisol;
3,5-di-t-butyl-4-hydroxyphenyl stearate;
bis(3,5-di-t-butyl-4-hydroxyphenyl)adipate.

1.4 Tocopherols such as, for example:
α-tocopherol, β-tocopherol, γ-tocopherol, δ-tocopherol and their mixtures (Vitamin E).

1.5 Hydroxylated thiodiphenyl ethers such as, for example:

2,2'-thiobis-(6-t-butyl-4-methylphenol);
2,2'-thiobis-(4-octylphenol);
4,4'-thiobis-(6-t-butyl-3-methylphenol);
4,4'-thiobis-(6-t-butyl-2-methylphenol);
4,4'-thiobis-(3,6-di-sec-amylphenol);
4,4'-bis-(2,6-dimethyl-4-hydroxyphenyl)disulfide.

1.6 Alkylidene-bisphenols such as, for example:

2,2'-methylenebis-(6-t-butyl-4-methylphenol);
2,2'-methylenebis-(6-t-butyl-4-ethylphenol);
2,2'-methylenebis[4-methyl-6-(α-methylcyclohexyl)phenol];
2,2'-methylenebis(4-methyl-6-cyclohexylphenol);
2,2'-methylenebis(6-nonyl-4-methylphenol);
2,2'-methylenebis(4,6-di-t-butylphenol);
2,2'-ethylidenebis(4,6-di-t-butylphenol);
2,2'-ethylidenebis(6-t-butyl-4-isobutylphenol);
2,2'-methylenebis[6-(α-methylbenzyl)-4-nonylphenol];
2,2'-methylenebis[6-(α,α-dimethylbenzyl)-4-nonylphenol];
4,4'-methylenebis(2,6-di-t-butylphenol);
4,4'-methylenebis(6-t-butyl-2-methylphenol);
1,1-bis-(5-t-butyl-4-hydroxy-2-methylphenyl)butane;
2,6-bis-(3-t-butyl-5-methyl-2-hydroxybenzyl)-4-methylphenol;
1,1,3-tris-(5-t-butyl-4-hydroxy-2-methylphenyl)butane;
1,1-bis-(5-t-butyl-4-hydroxy-2-methyl-phenyl)-3-n-dodecylmercaptobutane;
ethyleneglycol bis[3,3-bis(3'-t-butyl-4'-hydroxyphenyl)butyrate];
bis(3-t-butyl-4-hydroxy-5-methylphenyl)dicyclopentadiene;
bis[2-(3'-t-butyl-2'-hydroxy-5'-methylbenzyl)-6-t-butyl-4-methylphenyl]terephthalate;
1,1-bis(3,5-dimethyl-2-hydroxyphenyl)butane;
2,2-bis(3,5-di-t-butyl-4-hydroxyphenyl)propane;
2,2-bis(5-t-butyl-4-hydroxy-2-methylphenyl)-4-n-dodecylmercaptobutane;
1,1,5,5-tetra(5-t-butyl-4-hydroxy-2-methylphenyl)pentane.

1.7 Benzyl compounds containing O, N or S such as, for example:
3,5,3',5'-tetra-t-butyl-4,4'-dihydroxydibenzyl ether;
octadecyl-4-hydroxy-3,5-dimethylbenzylmercaptoacetate;
tris(3,5-di-t-butyl-4-hydroxybenzyl)amine;
bis(4-t-butyl-3-hydroxy-2,6-dimethylbenzyl)dithioterephthalate;
bis(3,5-di-t-butyl-4-hydroxybenzyl)sulfide;
iso-octyl-3,5-di-t-butyl-4-hydroxybenzylmercaptoacetate;

1.8 Hydroxybenzylated malonates such as, for example:
dioctadecyl-2,2-bis(3,5-di-t-butyl-2-hydroxybenzyl)malonate;
dioctadecyl-2-(3-t-butyl-4-hydroxy-5-methylbenzyl)malonate;
didodecylmercaptoethyl-2,2-bis(3,5-di-t-butyl-4-hydroxybenzyl)malonate;
bis[4-(1,1,3,3-tetramethylbutyl)phenyl]-2,2-bis(3,5-di-t-butyl-4-hydroxybenzyl)malonate.

1.9 Aromatic hydroxybenzyl compounds such as, for example:
1,3,5-tris(3,5-di-t-butyl-4-hydroxybenzyl)-2,4,6-trimethylbenzene;
1,4-bis-(3,5-di-t-butyl-4-hydroxybenzyl)-2,3,5,6-tetramethylbenzene;
2,4,6-tris(3,5-di-t-butyl-4-hydroxybenzyl)phenol.

1.10 Triazine compounds such as, for example:
2,4-bis(octylmercapto)-6-(3,5-di-t-butyl-4-hydroxyaniline)-1,3,5-triazine;
2-octylmercapto-4,6-bis(3,5-di-t-butyl-4-hydroxyaniline)-1,3,5-triazine;
2-octylmercapto-4,6-bis(3,5-di-t-butyl-4-hydroxyphenoxy)-1,3,5-triazine;
2,4,6-tris-(3,5-di-t-butyl-4-hydroxyphenoxy)-1,2,3-triazine;
1,3,5-tris(3,5-di-t-butyl-4-hydroxybenzyl)isocyanurate;
1,3,5-tris(4-t-butyl-3-hydroxy-2,6-dimethylbenzyl)isocyanurate;
2,4,6-tris-(3,5-di-t-butyl-4-hydroxyphenylethyl)-1,3,5-triazine;
1,3,5-tris (3,5-di-t-butyl-4-hydroxyphenylpropionyl) hexahydro-1,3,5-triazine;
1,3,5-tris-(3,5-dicyclohexyl-4-hydroxybenzyl)isocyanurate.

1.11 Benzylphosphonates such as, for example:
dimethyl-2,5-di-t-butyl-4-hydroxybenzylphosphonate;
diethyl-3,5-di-t-butyl-4-hydroxybenzylphosphonate;
dioctadecyl-3,5-di-t-butyl-4-hydroxybenzylphosphonate;
dioctadecyl-5-t-butyl-4-hydroxy-3-methylbenzylphosphonate;
calcium salts of monoethyl ester of 3,5-di-t-butyl-4-hydroxybenzylphosphonic acid.

1.12 Acylaminophenols such as, for example:
4-hydroxylauranilide;
4-hydroxystearanilide;
octyl-N-(3,5-di-t-butyl-4-hydroxyphenyl)carbamate.

1.13 Esters of β-(3,5-di-t-butyl-4-hydroxyphenyl) propionic acid with monohydric or polyhydric alcohols such as, for example: methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)

oxamide, 3-thioundecanol, 3-thiopentadecanol, trimethylhexandiol, trimethylolpropane, 4-hydroxymethyl-1-phospho-2,6,7-trioxabicyclo[2.2.2]octane.

1.14 Esters of β-(5-t-butyl-4-hydroxy-3-methylphenyl) propionic acid with monohydric or polyhydric alcohols such as, for example:

methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thioundecanol, 3-thiopentadecanol, trimethylhexandiol, trimethylolpropane, 4-hydroxymethyl-1-phospho-2,6,7-trioxabicyclo[2.2.2]octane.

1.15 Esters of β-(3,5-dicyclohexyl-4-hydroxyphenyl) propionic acid with monohydric or polyhydric alcohols such as, for example:

methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thioundecanol, 3-thiopentadecanol, trimethylhexandiol, trimethylolpropane, 4-hydroxymethyl-1-phospho-2,6,7-trioxabicyclo[2.2.2]octane.

1.16 Esters of (3,5-di-t-butyl-4-hydroxyphenyl)acetic acid with monohydric or polyhydric alcohols such as, for example:

methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thioundecanol, 3-thiopentadecanol, trimethylhexandiol, trimethylolpropane, 4-hydroxymethyl-1-phospho-2,6,7-trioxabicyclo[2.2.2]octane.

1.17 Amides of β-(3,5-di-t-butyl-4-hydroxyphenyl) propionic acid such as, for example:

N,N'-bis(3,5-di-t-butyl-4-hydroxyphenylpropionyl) hexamethylenediamine;
N,N'-bis(3,5-di-t-butyl-4-hydroxyphenylpropionyl) trimethylenediamine;
N,N'-bis(3,5-di-t-butyl-4-hydroxyphenylpropionyl) hydrazine.

2. Ultra-violet Ray and Light Stabilizers 2.1 Derivatives of 2-(2'-hydroxyphenyl)benzotriazoles such as, for example:

2-(2'-hydroxy-5'methylphenyl)benzotriazole;
2-(3',5'-di-t-butyl-2'-hydroxyphenyl)benzotriazole;
2-(5'-t-butyl-2'-hydroxyphenyl)benzotriazole;
2-[2'-hydroxy-5'-(1,1,3,3-tetramethylbutyl)phenyl] benzotriazole;
2-(3',5'-di-t-butyl-2'-hydroxyphenyl)-5-chlorobenzotriazole;
2-(3'-t-butyl-2'-hydroxy-5'-methylphenyl)-5-chlorobenzotriazole;
2-(3'-sec-butyl-5'-t-butyl-2'-hydroxyphenyl)benzotriazole;
2-(2'-hydroxy-4'-octyloxyphenyl)-benzotriazole;
2-(3',5'-di-t-amyl-2'-hydroxyphenyl)-benzotriazole;
2-[3',5'-bis(α,α-dimethylbenzyl)-2'-hydroxyphenyl] benzotriazole;
mixtures of 2-[3'-t-butyl-2'-hydroxy-5'-(2-octyloxycarbonylethyl)phenyl)-5-chorobenzotriazole, 2-[3'-t-butyl-5'-(2-(2-ethylhexyloxy)carbonylethyl)2'-hydroxyphenyl]-5-chlorobenzotriazole, 2-[3'-t-butyl-2'-hydroxy-5'-(2-methoxycarbonylethyl)phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5'-(2-octyloxycarbonylethyl)phenyl] benzotriazole, 2-[3'-t-butyl-5'-(2-(2-ethylhexyloxy) carbonylethyl)-2'-hydroxyphenyl)benzotriazole, 2-(3'-dodecyl-2'-hydroxy-5'-methylphenyl)benzotriazole and 2-[3'-t-butyl-2'-hydroxy-5'-(2-iso-octyloxycarbonylethyl) phenyl]benzotriazole, 2,2'-methylene-bis(4-(1,1,3,3-tetramethylbutyl)-6-benzotriazol-2-yl-phenol]; esterification product of 2-[3'-t-butyl-5'-(2-methoxycarbonylethyl)-2'-hydroxyphenyl]-2H-benzotriazole with polyethylene glycol 300;
[R—CH$_2$CH$_2$—COO(CH$_2$)$_3$]$_2$ wherein R=3'-t-butyl-4-hydroxy-5'-2H-benzotriazol-2-yl-phenyl.

2.2 Derivatives of 2-hydroxybenzophenones such as, for example: 4-hydroxy-; 4-methoxy-; 4-octyloxy-; 4-decyloxy-; 4-dodecyloxy-; 4-benzyloxy-; 4,2',4'-trihydroxy-; 2'-hydroxy-4,4'-dimethoxy.

2.3 Esters of benzoic acids, optionally substituted, such as, for example: phenyl salicylate, 4-t-butylphenyl salicylate, octylphenyl salicylate, benzoyl-resorcinol, bis(4-t-butylbenzoyl)-resorcinol, dibenzoyl-resorcinol, 2,4-di-t-butylphenyl-3,5-di-t-butyl-4-hydroxybenzoate, hexadecyl-3,5-di-t-butyl-4-hydroxybenzoate, octadecyl-3,5-di-t-butyl-4-hydroxybenzoate, 2-methyl-4,6-di-t-butyl-phenyl-3,5-di-t-butyl-4-hydroxybenzoate.

2.4 Acrylates such as, for example, ethyl or isoctyl 60-cyano-β,β-diphenylacrylate; methyl α-carbomethoxycinnamate, methyl or butyl α-cyano-β-methyl-p-methoxycinnamate, methyl α-carbomethoxy-p-methoxycinnamate, N-(β-carbomethoxy-β-cyanovinyl)-2-methylindoline.

2.5 Nickel compounds such as, for example, complexes of 2,2'-thio-bis-[4-(1,1,3,3-tetramethylbutyl)phenol], for example 1:1 or 1:2 complexes, with or without additional ligands such as n-butylamine, triethanolamine or N-cyclohexyldiethanolamine, nickel dibutyldithiocarbamate, nickel salts of monoalkyl esters of 4-hydroxy-3,5-di-t-butyl-benzyl-phosphonic acid, such as methyl or ethyl esters, nickel complexes with ketoximes such as 2-hydroxy-4-methylphenyl undecyl ketoxime, nickel complexes of 1-phenyl-4-lauroyl-5-hydroxypyrazol with or without additional ligands.

2.6 Sterically hindered amines such as, for example:
bis(2,2,6,6-tetramethyl-piperidyl)sebacate;
bis(2,2,6,6-tetramethyl-piperidyl)succinate;
poly-methylpropyl-3-oxy[4-(2,2,6,6-tetramethyl) piperidinyl]siloxane;
bis(1,2,2,6,6-pentamethyl-piperidyl)sebacate;
bis(1,2,2,6,6-pentamethyl-piperidyl)n-butyl-3,5-di-t-butyl-4-hydroxybenzylmalonate;
condensation product between 1-(2-hydroxyethyl)-2,2,6,6-tetra-4-hydroxypiperidine and succinic acid;
condensation product between N,N'-bis(2,2,6,6-tetramethyl-4-piperidyl)hexamethylenediamine and 4-t-octylamino-2,6-dichloro-1,3,5-triazine;
tris(2,2,6, 6-tetramethyl-4-piperidyl)nitrilotriacetate;
tetrakis(2,2,6,6-tetramethyl-4-piperidyl)-1,2,3,4-butanetetracarboxylate;
1,1'-(1,2-ethanodiyl)bis(3,3,5,5-tetramethylpiperazinone;
4-benzoyl-2,2,6,6-tetramethylpiperidine;
4-stearyloxy-2,2,6,6-tetramethylpiperidine;
bis(1,2,2,6,6-pentamethylpiperidyl)-2-n-butyl-2-(2-hydroxy-3,5-di-t-butylbenzyl)malonate;
3-n-octyl-7,7,9,9-tetramethyl-1,3,8-triazaspiro[4.5]decan-2,4-dione;

bis(1-octyloxy-2,2,6,6-tetramethylpiperidyl)sebacate;
bis(1-octyloxy-2,2,6,6-tetramethylpiperidyl)succinate;
condensation product between N,N'-bis(2,2,6,6-tetramethyl-4-piperidyl)hexamethylenediamine and 4-morpholine-2,6-dichloro-1,3,5-triazine;
condensation product between 2-chloro-4,6-di-(4-n-butylamino-2,2,6,6-tetramethylpiperidyl)-1,3,5-triazine and 1,2-bis(3-aminopropylamino)ethane;
condensation product between 2-chloro-4,6-di-(4-n-butylamino-1,2,2,6,6-pentamethylpiperidyl)-1,3,5-triazine and 1,2-bis(3-aminopropylamino)ethane;
8-acetyl-3-dodecyl-7,7,9,9-tetramethyl-1,3,8-triazaspiro[4.5]decano-2,4-dione;
3-dodecyl-1-(2,2,6,6-tetramethyl-4-piperidyl)pyrrolidin-2,5-dione;
3-dodecyl-1-(1,2,2,6,6-pentamethyl-4-piperidyl)pyrrolidin-2,5-dione.

2.7 Oxamides such as, for example:
4,4'-dioctyloxyoxanilide;
2,2'-diethoxyoxanilide;
2,2'-dioctyloxy-5,5'-di-t-butoxanilide;
2,2'-didodecyloxy-5,5'-di-t-butoxanilide;
2-ethoxy-2'-ethyloxanilide;
N,N'-bis(3-dimethylaminopropyl)oxamide;
2-ethoxy-5-t-butyl-2'-ethoxanilide and its mixtures with 2-ethoxy-2'-ethyl-5,4'-di-t-butoxanilide; and mixtures of disubstituted ortho- and paramethoxy anilides and mixtures of disubstituted ortho and para-ethoxy anilides.

2.8 2-(2-hydroxyphenyl)-1,3,5-triazines such as, for example:
2,4,6-tris(2-hydroxy-4-octyloxyphenyl)-1,3,5-triazine;
2-(2-hydroxy-4-octyloxyphenyl)-4,6-bis(2,4-dimethylphenyl)-1,3,5-triazine;
2-(2,4-dihydroxyphenyl)-4,6-bis(2,4-dimethylphenyl)-1,3,5-triazine;
2,4-bis-(2-hydroxy-4-propyloxyphenyl)-6-(2,4-dimethylphenyl)-1,3,5-triazine;
2-(2-hydroxy)-4,6-bis(4-methylphenyl)-1,3,5-triazine;
2-(2-hydroxy-4-dodecyloxyphenyl)-4,6-bis(2,4-dimethylphenyl)-1,3,5-triazine;
2-[2-hydroxy-4-(2-hydroxy-3-butyloxypropoxy)phenyl]-4,6-bis(2,4-dimethyl)-1,3,5-triazine;
2-[2-hydroxy-4-(2-hydroxy-3-octyloxypropyloxy)phenyl]-4,6-bis(2,4-dimethyl)-1,3,5-triazine.

3. "Metal-deactivators" such as, for example: N,N-diphenyloxamide, N-salicylal-N'-salicyloyl-hydrazine, N,N'-bis(salicyloyl)hydrazine; N,N'-bis(3,5-di-t-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxallyl dihydrazide, N,N'-bis(salicyloyl)thiopropionyl dihydrazide.

4. Phosphites and phosphonites such as, for example: triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-t-butylphenyl)phosphite, diisodecyl pentaerythritol diphosphite, bis(2,4-di-t-butylphenyl) pentaerythritol diphosphite, bis(2,5-di-t-butyl-4-methylphenyl)pentaerythritol diphosphite, diisodecyloxypentaerythritol diphosphite, bis(2,4-di-t-butyl-6-methylphenyl)pentaerythritol diphosphite, bis[2,4,5-tris(t-butylphenyl)]pentaerythritol diphosphite, tristearyl sorbitol triphosphite, tetrakis-(2,4-di-t-butyl-phenyl)-4,4'-diphenylenediphosphonite, 5-iso-octyloxy-2,4,8,10-tetra-t-butyl-12H-di-benzo[d,g]-1,3,2-dioxaphosphocine, 6-fluoro-2,4,8,10-tetra-t-butyl-12-methyl-dibenzo[d,g]-1,3,2-dioxaphosphocine, bis(2,4-di-t-butyl-6-methylphenyl)methylphosphite, bis(2,4-di-t-butyl-6-methylphenyl)ethylphosphite.

5. Agents which are capable of destroying peroxides such as, for example, esters of β-thiodipropionic acid such as lauryl, stearyl, myristyl or tridecyl esters, mercaptobenzimidazole or zinc salt of 2-mercaptobenzimidazole, zinc dibutyldithiocarbamate, dioctadecyldisulfide pentaerythritol tetrakis (β-dodecylmercapto)propionate.

6. Stabilizers of polyamides such as, for example, copper salts combined with compounds of iodine and/or phosphorous, divalent manganese salts.

7. Basic co-stabilizers such as, for example: melamine, polyvinylpyrrolidone, dicyanodiamide, triallyl cyanurate, derivatives of urea, derivatives of hydrazine, amines, polyamides, polyurethanes, salts of alkaline metals and salts of earth-alkaline metals of fatty acids such as, for example, Ca-stearate, Zn-stearate, Mg-stearate, Mg-behenate, Na-ricinoleate, K-palmitate, antimonium-pyrocatecholate, tin-pyrocatecholate.

8. Nucleating agents such as, for example: 4-t-butylbenzoic acid, adipic acid, diphenylacetic acid.

9. Fillers and reinforcing agents such as, for example: calcium carbonate, silicates, glass fibres, asbestos, talc, kaolin, mica, barium sulfate, metal oxides and hydroxides, carbon black, graphite.

10. Other additives such as, for example: plasticizers, lubricants, emulsifying agents, pigments, optical brighteners, flame-retardants (for example, bromurates, chlorurates, phosphorates and phosphorous/halogen mixtures), antistatic agents, blowing agents, thiosynergizing agents such as, for example, dilauryl thiodipropionate or distearyl thiodipropionate.

11. Benzofuranones and indolinones such as, for ex.:
3-[4-(2-acetoxyethoxy)phenyl]-5,7-di-t-butylbenzofuran-2-one;
5,7-di-t-butyl-3-[4-(2-stearoyloxyethoxy)phenyl]benzofuran-2-one;
3,3'-bis[5,7-di-t-butyl-3-[4-(2-hydroxyethoxy)phenyl]benzofuran-2-one];
5,7-di-t-butyl-3-(4-ethoxyphenyl)benzofuran-2-one;
3-(4-acetoxy-3,5-dimethylphenyl)-5,7-di-t-butyl-benzofuran-2-one;
3-(3,5-dimethyl-4-pivaloyloxyphenyl)-5,7-di-t-butyl-benzofuran-2-one;
or those described in U.S. Pat. Nos. 4,325,863, 4,338,244, 5,175,312, 5,216,052, 5,252,643, 4,316,611, 4,316,622, 4,316,876 or in European patent applications 589.839 and 591.102.

Some illustrative but non-limiting examples are provided hereunder for a better understanding of the present invention and for its embodiment.

EXAMPLE 1

Preparation of Compound Nr. 1 having the formula:

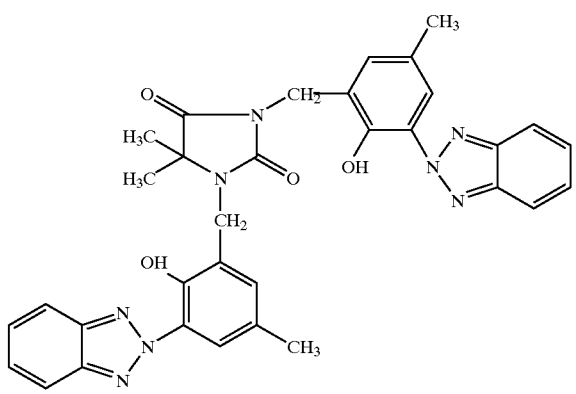

11.3 g (0.05 moles) of 2-(2'-hydroxy-5'-methyl) benzotriazole in 67 ml of concentrated sulfuric acid at 96% are charged into a 250 ml 4-necked flask, equipped with a mechanical stirrer, drip funnel, thermometer and condenser, and the temperature is maintained at −5° C. to 0° C. 10.27 g (0.065 moles) of an aqueous solution at 33% of 1-N-monomethylol-5,5-dimethylidanthoine is then slowly added dropwise in 30 minutes, the temperature being maintained at −5° C. to 0° C.

The above mixture is left to rise to 25° C. under stirring, is maintained at this temperature, continually under stirring, for 4 hours and is then heated to 70° C. for a further 8 hours. The raw product obtained is poured into 400 ml of water-ice, filtered and then washed to neutral pH.

15 g (0.041 moles) of a solid product is obtained which is reacted with 1.23 g (0.041 moles) of formaldehyde in the presence of 0.3 g (0.0028 moles) of sodium carbonate and 100 ml of methanol obtaining 16 g of a compound having formula (X):

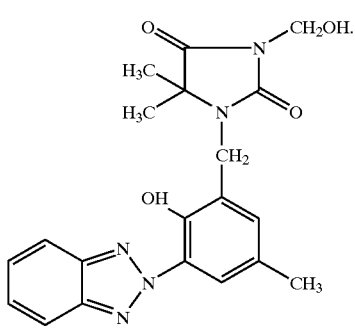

9 g (0.04 moles) of 2-(2'-hydroxy-5'-methyl)benzotriazole are poured into 70 ml of concentrated sulfuric acid at 96%, the temperature being maintained at between −5° C. and 0° C. 15.8 g (0.04 moles) of the compound having formula (X) obtained as described above are then slowly added.

The above mixture is left to rise to 25° C. under stirring, and is maintained at this temperature, continually under stirring, for 20 hours. The raw product obtained is poured into 400 ml of water-ice, filtered and then washed to neutral pH.

A solid is thus obtained, which is crystallized with 50 ml of 2-methoxyethanol. From this crystallization, 21 g (yield 86%) of a white powder corresponding to Compound Nr. 1 are obtained, having the following characteristics:

melting point (DSC): 229° C.

I.R. in nujols ($cm^{-1}$): 3100, 1770, 1714.

$^1$H-NMR (200 MHz, $CDCl_3$) δ(ppm): 1.4 (s, 6H); 2.36 (s, 3H); 2.38 (s, 3H); 4.8 (s, 2H); 4.9 (s, 2H); 7.0 (s, 1H); 7.2 (s, 1H); 7.4 (dd, 4H); 7.9 (dd, 4H); 8.1 (s, 2H); 11.4 (s, 1H); 11.6 (s, 1H).

$^{13}$C-NMR (50 MHz, $CDCl_3$) δ(ppm): 20.57; 20.63; 22.93; 36.53; 37.87; 62.22; 117.47; 120.63; 124.75; 125.10; 127.59; 127.72; 128.87; 129.41; 130.43; 131.48; 142.59; 144.95; 145.53; 155.80; 176.58.

Elemental analysis:

| ELEMENTAL ANALYSIS | C | $C_{33}H_{30}N_8O_4$ H | N |
|---|---|---|---|
| CALCULATED | 65.8% | 4.98% | 18.6% |
| FOUND | 65.2% | 4.88% | 18.3% |

EXAMPLE 2

Preparation of Compound Nr. 2 having the formula:

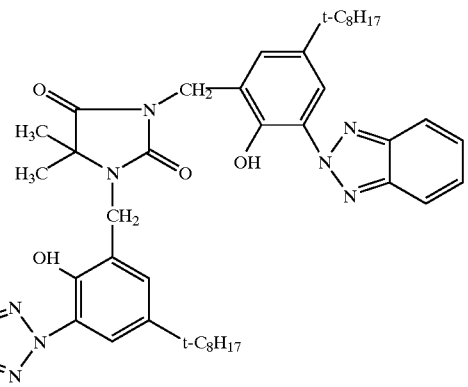

16.15 g (0.05 moles) of 2-(2'-hydroxy-5'-t-octyl) benzotriazole in 67 ml of concentrated sulfuric acid at 96% are charged into a 250 ml 4-necked flask, equipped with a mechanical stirrer, drip funnel, thermometer and condenser, and the temperature is maintained at −5° C. to 0° C. 10.27 g (0.065 moles) of an aqueous solution at 33% of 1-N-monomethylol-5,5-dimethylidanthoine is then slowly added dropwise in 30 minutes, the temperature being maintained at −5° C. to 0° C.

The above mixture is left to rise to 25° C. under stirring, is maintained at this temperature, continually under stirring, for 4 hours and is then heated to 70° C. for a further 8 hours. The raw product obtained is poured into 400 ml of water-ice, filtered and then washed to neutral pH.

19 g (0.041 moles) of a solid product is obtained which is reacted with 1.23 g (0.041 moles) of formaldehyde in the presence of 0.3 g (0.0028 moles) of sodium carbonate and 100 ml of methanol obtaining 20 g of a compound having formula (X'):

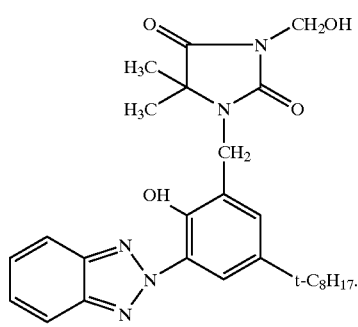

12.92 g (0.04 moles) of 2-(2'-hydroxy-5'-t-octyl) benzotriazole are poured into 70 ml of concentrated sulfuric acid at 96%, the temperature being maintained at between −5° C. and 0° C. 19.7 g (0.04 moles) of the compound having formula (X') obtained as described above are then slowly added.

The above mixture is left to rise to 25° C. under stirring, and is maintained at this temperature, continually under stirring, for 20 hours. The raw product obtained is poured into 400 ml of water-ice, filtered and then washed to neutral pH.

A solid is thus obtained, which is crystallized with 130 ml of n-octane. From this crystallization, 28 g (yield 88%) of a white powder corresponding to Compound Nr. 2 are obtained, having the following characteristics:

melting point: 92° C.

$^1$H-NMR (200 MHz, CDCl$_3$) δ(ppm): 0.65 (s, 9H); 0.73 (s, 9H); 1.33 (s, 6H); 1.38 (s, 6H); 1.41 (s, 6H); 1.69 (s, 2H); 1.76 (s, 2H); 4.79 (s, 2H); 4.96 (s, 2H); 7.4 (m, 6H); 7.9 (dd, 4H); 8.3 (d, J=1Hz; 2H); 11.57 (s, 1H); 11.63 (s, 1H).

$^{13}$C-NMR (50 MHz, CDCl$_3$) δ(ppm): 22.0; 31.6; 31.8; 37.0; 38.0; 38.5; 56.5; 57.0; 62.3; 117.5; 118.0; 124.5; 126.5; 127.7 127.9; 128.9; 129.3; 141.5; 142.0; 142.5; 144.9; 145.1; 155.4; 176.9.

EXAMPLE 3
Ultraviolet Ray Absorption Data $10^{-2}$ M solutions in chloroform of Compounds Nr. 1 and 2 obtained as described above, Tinuvin 900 produced and sold by Ciba Geigy and Mixxim BB/100 produced and sold by Fairmount, are prepared. These solutions are analyzed using a diode spectrophotometer of the type "hp 8452A Diode Array spectrophotometer" and the ε molar extinction coefficients at λ=400 nm are indicated in Table 1.

TABLE 1

| COMPOUND Nr. | ε (1.mol$^{-1}$.cm$^{-1}$) |
|---|---|
| 1 | 96 |
| 2 | 110 |
| Tinuvin 900 | 180 |
| Mixxim BB/100 | 253 |

$5·10^{-5}$ M solutions in chloroform of Compounds Nr. 1 and 2 obtained as described above, Tinuvin 900 produced and sold by Ciba Geigy and Mixxim BB/100 produced and sold by Fairmount, are also prepared. These solutions are analyzed using the above spectrophotometer and the molar extinction coefficients $\epsilon_1$ at λ=302 nm and $\epsilon_2$ at λ=342 nm are shown in Table 2.

TABLE 2

| COMPOUND Nr. | $\epsilon_1$ (1.mol$^{-1}$.cm$^{-1}$) | $\epsilon_2$ (1.mol$^{-1}$.cm$^{-1}$) |
|---|---|---|
| 1 | 29800 | 34100 |
| 2 | 30200 | 36400 |
| Tinuvin 900 | 17150 | 16120 |
| Mixxim BB/100 | 29792 | 29786 |

EXAMPLE 4
Thermogravimetric Data

Using a standard instrument for thermogravimetric analysis (TA Instrument Model 3000 of Mettler) the following isothermal and gravimetric data are determined relating to Compounds Nr. 1 and Nr. 2 which are compared with the data of Tinuvin 900 produced and sold by Ciba Geigy and Mixxim BB/100 produced and sold by Fairmount. The data obtained are shown in Table 3.

TABLE 3

| COMPOUND Nr. | ISOTHERM AT 280° C.; 18 Nl/h N$_2$; TIME IN MINUTES TO INDICATE LOSS IN WEIGHT OF THE STABILIZER | | SCANNING AT 10° C./min; 18 Nl/h N$_2$; TEMPERATURE IN ° C. TO INDICATE LOSS IN WT. OF STABILIZER | |
|---|---|---|---|---|
|  | 10% | 50% | 10% | 50% |
| 1 | >>60 | >60 | 361 | 395 |
| 2 | >>60 | >60 | 320 | 362 |
| Tinuvin 900 | 4 | 20 | 281 | 319 |
| Mixxim BB/100 | >60 | >60 | 390 | 443 |

EXAMPLE 5
Stabilization in Polycarbonate 20 g of bisphenol A polycarbonate are dissolved in 100 ml of methylene chloride, at room temperature under stirring. After several hours, when the polycarbonate has completely dissolved, 0.1 g of Compound Nr. 1 or Compound Nr. 2 or Tinuvin 900 or Mixxim BB/100 are added (addition equal to 0.5%). For comparative purposes a solution without light stabilizers is prepared.

Films with a thickness of 100 μm are prepared from the above solutions by casting.

The films obtained are subjected to accelerated aging in an Atlas CI 65 Weatherometer under the following conditions:

black panel temperature: 60° C.;

relative humidity: 50%.

Before beginning the aging and afterwards, at regular intervals, the yellow index (YI) of the above films is measured using the method ASTM E 313. The crushing time is also analyzed.

The results obtained are indicated in Table 4.

TABLE 4

| COMPOUND | EXPOSURE TIME (h) | | | | | | |
|---|---|---|---|---|---|---|---|
| Nr. | 0 | 250 | 500 | 600 | 800 | 1.000 | 1.500 |
| — | 0.4 | 4.0 | 12.4* | — | — | — | — |
| 1 | 0.3 | 3.0 | 5.0 | 8.0 | 9.5 | 10.6 | 12.6* |
| 2 | 0.5 | 3.6 | 5.8 | 8.7 | 9.3 | 10.9 | 12.7* |
| Tinuvin 900 | 0.4 | 3.2 | 6.0 | 9.5 | 10.8 | 12.0* | — |
| Mixxim BB/100 | 0.4 | 3.3 | 5.6 | 8.8 | 9.4 | 11.0 | 12.4* |

*crushing of sample.

What is claimed is:

1. A 2-(2'-hydroxyphenyl)benzotriazole having formula (I):

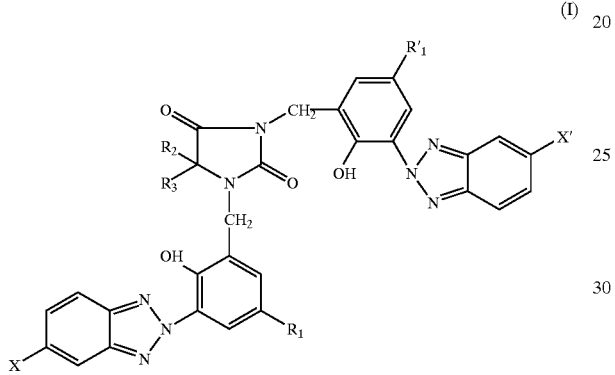

(I)

wherein:

X and X' are the same or different and represent a hydrogen atom; a halogen atom selected from the group consisting of chlorine and bromine; a linear or branched $C_1$–$C_{18}$ alkyl group; a linear or branched $C_1$–$C_{18}$ alkoxy group; and a cyano group;

$R_1$ and $R'_1$ are the same or different and represent a halogen atom selected from the group consisting of chlorine and bromine; a linear or branched $C_1$–$C_{18}$ alkyl group; a linear or branched $C_2$–$C_{18}$ alkenyl group; a linear or branched $C_2$–$C_{18}$ alkinyl group; a $C_5$–$C_{18}$ cycloalkyl group, said cycloalkyl group optionally substituted; a $C_7$–$C_{15}$ arylalkyl; a $C_6$–$C_{14}$ aryl group, said aryl group optionally substituted; a linear or branched $C_1$–$C_{18}$ alkoxy group; a group having the formula:

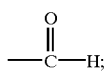

a —$COR_4$ group or a —$NR_5R_6$ group wherein $R_4$, $R_5$ and $R_6$ are the same or different and represent a linear or branched $C_1$–$C_{18}$ alkyl group; a linear or branched $C_2$–$C_{18}$ alkenyl group; a linear or branched $C_2$–$C_{18}$ alkinyl group; a $C_5$–$C_{18}$ cycloalkyl group, said cycloalkyl group optionally substituted; a $C_7$–$C_{15}$ arylalkyl; a $C_6$–$C_{14}$ aryl group, said aryl group optionally substituted;

or $R_1$ and $R'_1$ are the same or different and represent an ester group having formula (II), (III) or (IV):

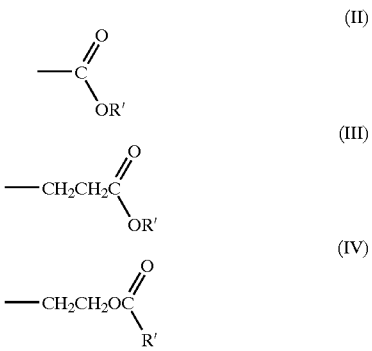

or an amide group having formula (V):

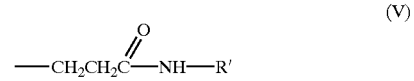

wherein R' represents a linear or branched $C_1$–$C_{18}$ alkyl group; a linear or branched $C_2$–$C_{18}$ alkenyl group; a linear or branched $C_2$–$C_{18}$ alkinyl group; a $C_5$–$C_{18}$ cycloalkyl group, said cycloalkyl group optionally substituted; a $C_7$–$C_{15}$ arylalkyl, a $C_6$–$C_{14}$ aryl group, said aryl group optionally substituted; a linear or branched $C_1$–$C_{18}$ alkoxy group; or $R_1$ and $R'_1$ are the same or different and represent an 4,4'-ethylidenebisphenol group having formula (VI):

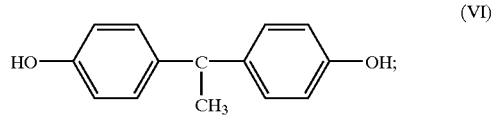

$R_2$ and $R_3$ are the same or different and represent a hydrogen atom; a linear or branched $C_1$–$C_{18}$ alkyl group; a phenyl group;

wherein the $C_5$–$C_{18}$ cycloalkyl group and the $C_6$–$C_{14}$ aryl group are optionally substituted with a halogen atom selected from the group consisting of chlorine and bromine; a linear or branched $C_1$–$C_{18}$ alkyl; a linear or branched $C_2$–$C_{18}$ alkenyl group; a linear or branched $C_2$–$C_{18}$ alkinyl group; an OH group, a NH group; or a SH group.

2. The 2-(2'-hydroxyphenyl)benzotriazole having formula (I) according to claim 1, wherein the $C_1$–$C_{18}$ alkyl group is methyl, ethyl, propyl, isopropyl, n-butyl, sec-butyl, t-butyl, t-amyl, 2-ethylhexyl, n-octyl, 1,1,3,3-tetramethylbutyl, n-dodecyl, 1,1,7,7-tetramethyloctyl or n-octadecyl.

3. The 2-(2'-hydroxyphenyl)benzotriazole having formula (I) according to claim 1, wherein the $C_2$–$C_{18}$ alkenyl group is vinyl, propylene, butylene, pentylene or hexylene.

4. The 2-(2'-hydroxyphenyl)benzotriazole having formula (I) according to claim 1, wherein the $C_2$–$C_{18}$ alkinyl group is acetylene, propyne, butyne or 2-butyne.

5. The 2-(2'-hydroxyphenyl)benzotriazole having formula (I) according to claim 1, wherein the $C_5$–$C_{18}$ cycloalkyl group, optionally substituted, is cyclohexyl, cyclopentyl or methylcyclohexyl.

6. The 2-(2'-hydroxyphenyl)benzotriazole having formula (I) according to claim 1, wherein the $C_7$–$C_{15}$ arylalkyl is benzyl or 2-phenylethyl.

7. The 2-(2'-hydroxyphenyl)benzotriazole having formula (I) according to claim 1, wherein the $C_6$–$C_{14}$ aryl group, optionally substituted, is phenyl, naphtyl, anthracenyl or 2-hydroxyphenyl.

8. The 2-(2'-hydroxyphenyl)benzotriazole having formula (I) according to claim 1, wherein the $C_1$–$C_{18}$ alkoxy group is methoxy, ethoxy, propoxy or n-butoxy.

9. The 2-(2'-hydroxyphenyl)benzotriazole according to claim 1, having the formula:

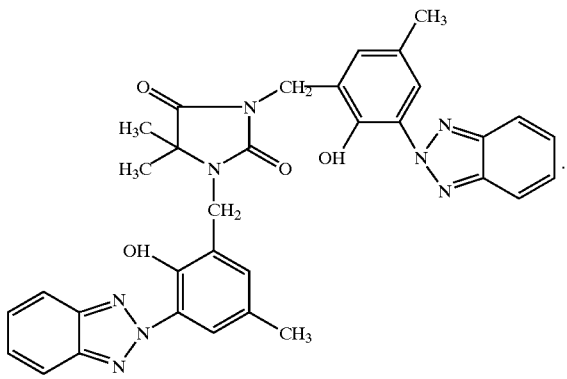

10. The 2-(2'-hydroxyphenyl)benzotriazole according to claim 1, having the formula:

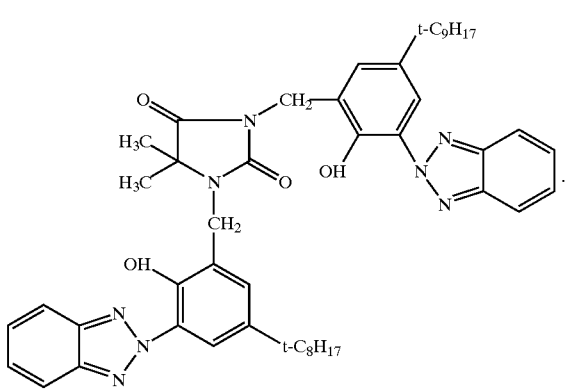

11. A process for the preparation of the 2-(2'-hydroxyphenyl)benzotriazole having formula (I) according to claim 1, which consists of reacting a 2-(2'-hydroxyphenyl)benzotriazole having formula (VIIA) or (VIIB):

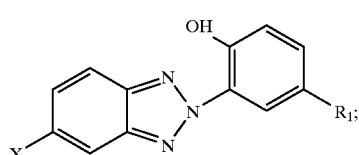

(VIIA)

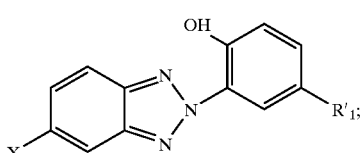

(VIIB)

wherein X, X', $R_1$ and $R'_1$ have the same meanings described above, with a 2,4-imidazolidinedione-1-monomethylol having formula (VIII):

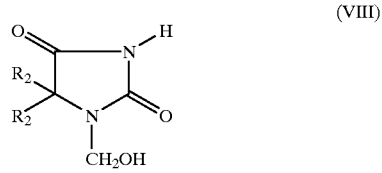

(VIII)

wherein $R_2$ and $R_3$ have the same meanings described above, in the presence of concentrated sulfuric acid, at a concentration ranging from 70% to 98%, at a temperature ranging from −5° C. to +30° C., obtaining a raw product from which an intermediate compound having formula (IXA) or (IXB), is isolated:

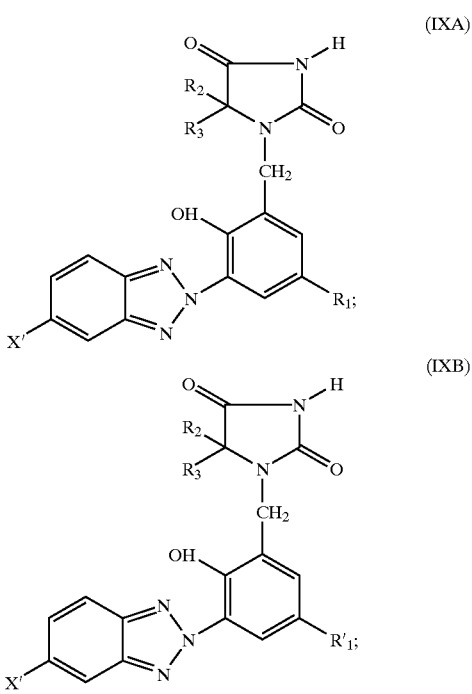

wherein X, X', $R_1$ and $R'_1$ have the same meanings described above, by dripping the raw product into water-ice and removing the solid obtained by filtration followed by washing and crystallization in the presence of an inert organic solvent.

12. The process according to claim 11, wherein the inert organic solvent used for effecting the crystallization is a linear or cyclic aliphatic hydrocarbon, an aromatic hydrocarbon, an alcohol, a chlorinated aromatic solvents, a ketone, or a monoalkyl ether of ethylene glycol.

* * * * *

UNITED STATES PATENT AND TRADEMARK OFFICE
CERTIFICATE OF CORRECTION

PATENT NO. : 6,452,018 B1
DATED : September 17, 2002
INVENTOR(S) : Riva et al.

It is certified that error appears in the above-identified patent and that said Letters Patent is hereby corrected as shown below:

<u>Title page, Item [54] and Column 1, lines 1-4,</u>
should read:

-- [54] S- (2' -HYDROXYPHENYL) BENZOTRIAZOLES CONTAINING A 2,4-IMIDAZOLIDINEDIONE GROUP AND PROCESS FOR THEIR PREPARATION --

<u>Title page,</u>
Item [73], should read:

-- [73] Assignee: Great Lakes Chemical Italia S.R.L., Milan (IT) --

Signed and Sealed this

Eleventh Day of March, 2003

JAMES E. ROGAN
*Director of the United States Patent and Trademark Office*